(12) United States Patent
Felix-Faure et al.

(10) Patent No.: US 8,882,726 B2
(45) Date of Patent: Nov. 11, 2014

(54) DRUG DELIVERY DEVICE WITH SAFE CONNECTION MEANS

(75) Inventors: Catherine Felix-Faure, Grenoble (FR); Benoit Guillard, Grenoble (FR); Michel Bosshardt, Claix (FR); Frédéric Perot, Saint Paul de Varces (FR)

(73) Assignee: Becton Dickinson France, Le Pont-de-Claix (FR)

( * ) Notice: Subject to any disclaimer, the term of this patent is extended or adjusted under 35 U.S.C. 154(b) by 45 days.

(21) Appl. No.: 13/583,352

(22) PCT Filed: Mar. 10, 2010

(86) PCT No.: PCT/IB2010/000943
§ 371 (c)(1),
(2), (4) Date: Dec. 14, 2012

(87) PCT Pub. No.: WO2011/110888
PCT Pub. Date: Sep. 15, 2011

(65) Prior Publication Data
US 2013/0178806 A1    Jul. 11, 2013

(51) Int. Cl.
*A61M 5/00* (2006.01)
*A61M 39/10* (2006.01)
*A61M 5/34* (2006.01)

(52) U.S. Cl.
CPC ............ *A61M 39/1011* (2013.01); *A61M 5/347* (2013.01); *A61M 39/10* (2013.01); *A61M 5/345* (2013.01); *A61M 2039/1044* (2013.01); *A61M 2039/1066* (2013.01); *A61M 2039/1077* (2013.01); *Y10S 604/905* (2013.01)
USPC .......................................... 604/257; 604/905

(58) Field of Classification Search
CPC ................... A61M 2039/1033; A61M 39/10; A61M 5/347
USPC ................................................... 604/257, 905
See application file for complete search history.

(56) References Cited

U.S. PATENT DOCUMENTS

| 5,649,637 A * | 7/1997 | Weiler ......................... 215/251 |
| 2004/0238776 A1 * | 12/2004 | Peters et al. ................ 251/149.1 |
| 2009/0171322 A1 * | 7/2009 | Kurimoto et al. ............. 604/533 |

FOREIGN PATENT DOCUMENTS

| EP | 1432468 A2 | 6/2004 |
| WO | 03020361 A2 | 3/2003 |
| WO | 2008014436 A2 | 1/2008 |

* cited by examiner

*Primary Examiner* — Nicholas Lucchesi
*Assistant Examiner* — Leah Stohr
(74) *Attorney, Agent, or Firm* — The Webb Law Firm (57) ABSTRACT

The present invention relates to a drug delivery device defining a reservoir for containing a product, having a distal end comprising an end-piece defining a channel for the transfer of the product from the reservoir, said drug delivery device comprising means for coupling said end-piece with a connector, said coupling means comprising a collar defined around a portion of the end-piece and extending from the distal end, said coupling means comprising connection means connectable to said collar, said connection means comprising a tubular wall portion having an interface defined thereon for engagement with an internal face of said collar, and a retaining hook having engagement means engageable with at least part of an external face of said collar when said connection means is connected to said collar.

13 Claims, 5 Drawing Sheets

DRUG DELIVERY DEVICE WITH SAFE CONNECTION MEANS

BACKGROUND OF THE INVENTION

1. Field of the Invention

The present invention relates to a drug delivery device having an end-piece surrounded by a collar and specific coupling means for coupling said end-piece to a connector.

2. Description of Related Art

Drug delivery devices usually comprise a hollow body forming a reservoir for containing a medical product. In addition, the distal end of the body forming the reservoir usually comprises an end-piece in which an axial passageway is arranged through which the said product is ejected from the reservoir.

In this application, the distal end of a component or of a device must be understood as meaning the end furthest from the hand of the user and the proximal end must be understood as meaning the end closest to the hand of the user.

Moreover, the reservoir and end-piece of a drug delivery device may be made of various materials such as glass or plastic. When it is known that the stability of the product stored in the reservoir is not impacted by the plastic nature of the wall of the reservoir, it is desirable to have a drug delivery device made of plastic materials, so as to avoid the common risks associated with the handling of glass material. Actually, when drug delivery devices made of glass material happen to break, not only the product they may contain is lost, but the resulting bits of glass material constitute danger for the persons who happen to be around. Moreover, the product lost may also generate a danger when such product is for example a toxic drug.

It is also desirable to have drug delivery devices made of plastic materials when these drug delivery devices are prefilled with the product and provided to the final user in a prefilled state: risks of breaking the drug delivery device during the various operation it is submitted to before use, such as the steps of prefilling, sterilization, packaging, transport, storage, are therefore substantially limited.

The handling of products, such as liquid medicine, in particular for a parenteral administration to a patient which is carried out via a perfusion device, as often in hospitals or in emergency situations, implies, in a general manner, the use of connectors, such as IV (Intra Veinous) connectors which link the drug delivery device, containing the product to be delivered, to the vein of the patient, usually via an IV line. Of course, the drug delivery device, in particular its end-piece and the connector must be assembled together correctly and securely.

In this view, the drug delivery device usually comprises an external collar surrounding the end-piece, this collar being intended to be connected to a connector so as to facilitate the transfer of the product from the end-piece of the drug delivery device to the connector, and then in the IV line.

At the time the connector is connected to the collar, the collar is submitted to a stress resulting from the force applied in order to connect the connector thereon. The intensity of the force applied may vary depending on the way the connector is connected on the collar: for example, the connector may be connected to the collar by force fitting of by screwing. The intensity of the force applied also depends on the user. As a consequence, the stress to which the collar is submitted to when the connector is connected thereon is not controllable.

Moreover, problems have been reported concerning the assembling of IV connectors to some types of drug delivery devices, in particular for drug delivery devices having their collar as described above made of plastic material such as cycloolefin polymers and/or copolymers. In particular, it happens that the collar surrounding the end-piece of the drug delivery device breaks at the time it is submitted to the necessary stress for connecting the connector thereon, for example by screwing. In such a case, the connector is not securely and correctly connected to the end-piece of the drug delivery device, and the administration of the medicine is made impossible or, at best, delayed. Moreover, such a phenomenon may also cause a risk of syphoning effect, ie uncontrolled delivery of drug due to difference of height between the drug delivery device and the catheter, which are both linked with the IV line.

SUMMARY OF THE INVENTION

It is nevertheless desirable to have drug delivery devices made of plastic material such as cycloolefin polymers and/or copolymers: indeed, such material is useful for the manufacture of prefilled drug delivery devices because it preserves the stability of the product stored in the drug delivery device. Such material is also very convenient because it shows high transparency for visual control of the drug. It also shows a high geometrical stability when it is subjected to high pressure in the drug delivery device.

Also, it may happen that the collar, between the time the drug delivery device is provided to the user and the time the connector is connected thereon, be degraded in one way or the other, for example by being contacted by some product in excess dripping from the end-piece at the time the user completes a purge. In such a case, the resulting connection between the connector and the collar is not reliable and may break, either at the time of connection of connector, during use, or at the time the connector is disconnected from the delivery device after use.

One aspect of the invention is to provide a drug delivery device having an end-piece surrounded by a collar, with very limited risks that the collar breaks at the time the connector is connected to, or disconnected from, the end-piece, regardless of the variation of intensity of the force that may be applied by a user for completing the connection step and regardless of the fact that the collar may have been contacted by a potential degrading product before the connection step.

One aspect of the present invention is a drug delivery device having a distal end comprising an end-piece defining a channel providing a passageway for the transfer of the product from the reservoir, said drug delivery device comprising coupling means for coupling said end-piece with a connector, said coupling means comprising a collar defined around a portion of the end-piece and extending from the distal end, said coupling means further comprising connection means connectable to said collar and for coupling the end-piece with a connector, said connection means comprising a tubular wall portion having an interface defined thereon for engagement with an internal face of said collar, said connection means further comprising a retaining hook having engagement means engageable with at least part of an external face of said collar when said connection means is connected to said collar.

Thanks to the structure of the coupling means, and in particular the connection means, of the device of the invention, the drug delivery device of the invention allows the coupling and the uncoupling of a connector onto its end-piece with very limited risks that the collar breaks: in particular, whatever the way the connector is coupled to the collar and end-piece, for example by force fitting or by screwing, the connection means absorbs the stress applied and prevents the collar from being damaged or or from breaking.

Moreover, the drug delivery device further allows a safe coupling of the connector to the end-piece, even in the case the collar has been contacted by some product in excess dripping from the end-piece after the user has completed a purge for example. Indeed, it may happen that, after a user has voluntarily ejected from the end-piece a minimal portion of the product contained in the reservoir in order to purge the drug delivery device before use, some tiny drops of the product contact the outer surface of the end-piece and/or the inner face of the collar: in the drug delivery devices of the prior art, such a phenomenon may degrade the collar and cause an unsafe and unreliable coupling between the collar, and thus the end-piece, and the connector.

Thanks to the structure of the connections means of the device of the invention, the drug delivery device of the invention allows a safe coupling between the end-piece and the connector, even in the case the collar has been previously contacted by some product coming from the reservoir.

In embodiments, the connection means is made of a polyolefines material selected from the group comprising polyethylene, linear low density polyethylene, polypropylene and mixtures thereof. Connection means made of such material have a strength preventing them from breaking when they are submitted to the force applied by the user at the time he couples the connector to the end-piece. Moreover, because the connection means comprise a tubular wall portion having an interface defined thereon for engagement with an internal face of the collar and a retaining hook having engagement means engageable with at least part of an external face of said collar, the force applied on the collar at the time the connector is coupled to the end-piece, is distributed over both the tubular wall and the collar: as a consequence, the collar is protected and does not break at the the time the connector is coupled to the end-piece. Moreover, tubular walls made of such material as polyolefines allow a safe coupling of the connector to the end-piece, even in the case some product in excess has dripped from the end-piece after the user has completed a purge for example.

The tubular wall may be fixed to said internal face of said collar with fixing means selected in the group comprising overmoulding, snap-fastening, screwing, welding, force fitting and combinations thereof. In embodiments, the interface is selected from the group consisting of overmoulding means, snap-fastening means, screwing means, welding means, force fitting means and combinations thereof.

In embodiments, said collar is made of a material selected from cycloolefin polymers, cycloolefin copolymers and mixtures thereof. Such a material is less likely to break than glass for example.

In embodiments, said retaining hook is a discontinuous ring extending from said tubular wall and covering part of the distal region of the outer face of the collar, when said connection means is connected to said collar. Alternatively, said retaining hook is a continuous ring extending from said tubular wall and covering the distal region of the outer face of the collar, when said connection means is connected to said collar. As seen above, the location of the retaining hook, close to at least part of the external face of the collar, allows the force applied on the distal end of the drug delivery device at the time the connector is coupled to be distributed on a plurality of elements, thereby releasing the force the collar is submitted to and preventing said collar to be degraded.

In embodiments, the inner face of said tubular wall is provided with a thread. Such a thread is usually intended to cooperate with an external thread located on the connector in order to screw the connector to the drug delivery device.

In embodiments, the inner face of said collar has a thread defined thereon engageable with said interface.

In embodiments, said connection means further comprises a tip having a duct defined therethrough, and an outer ring defined around said tip, said duct being axially aligned with said channel when said connection means is connected to said collar. In such embodiments, the inner face of said outer ring may have a thread defined thereon. The thread of the inner face of the outer ring is usually intended to cooperate with an external thread of the connector to be coupled to the end-piece of the drug delivery device.

In embodiments, said connection means is threadedly connectable with said collar. In such embodiments, for example, the internal face of said collar may be provided with a thread, and the outer face of said tubular wall may be provided with at least one outer rim able to cooperate with said thread so as to screw said tubular wall within said collar. For example, said outer face of said tubular wall may be provided with four outer rims regularly spaced in the axial direction one from the other, so that the four rims cooperate with said thread so as to screw said tubular wall within said collar. Such an embodiment allows a better distribution of the effort on the tubular wall when said tubular wall is sewed on the collar. The collar is therefore less submitted to a force likely to damage and/or break it.

In embodiments, said external face has defined thereon stopping means for preventing removal of said connection means from said collar, when said connection means is connected with said collar. The stopping means may cooperate with the engagement means of the retaining hook for preventing removal of said connection means from said collar, when said connection means is connected with said collar. For example, said external face has defined therein longitudinal ridges having sloped surfaces engageable with longitudinal projections defined on the retaining hook, so as to allow said connection means to be threadedly connected to said collar, and so as to prevent said connection means from being threadedly removed from said collar.

Such embodiments also allow a better fixing of the tubular wall onto the collar: in particular, not only the tubular wall is blocked in rotation with respect to the collar but it is also blocked in the axial direction with respect to the collar.

In other embodiments, said tubular wall is snap-fastened within said collar.

In embodiments, said reservoir, end-piece and collar are unitarily formed from a material selected from cycloolefin polymers, cycloolefin copolymers and mixtures thereof. As seen above, such a material is particularly useful in view of its high transparency, high geometrical stability and in terms of safety.

BRIEF DESCRIPTION OF THE DRAWINGS

The device of the invention will now be further described in reference to the following description and attached drawings in which.

DETAILED DESCRIPTION OF THE INVENTION

Figure 1:
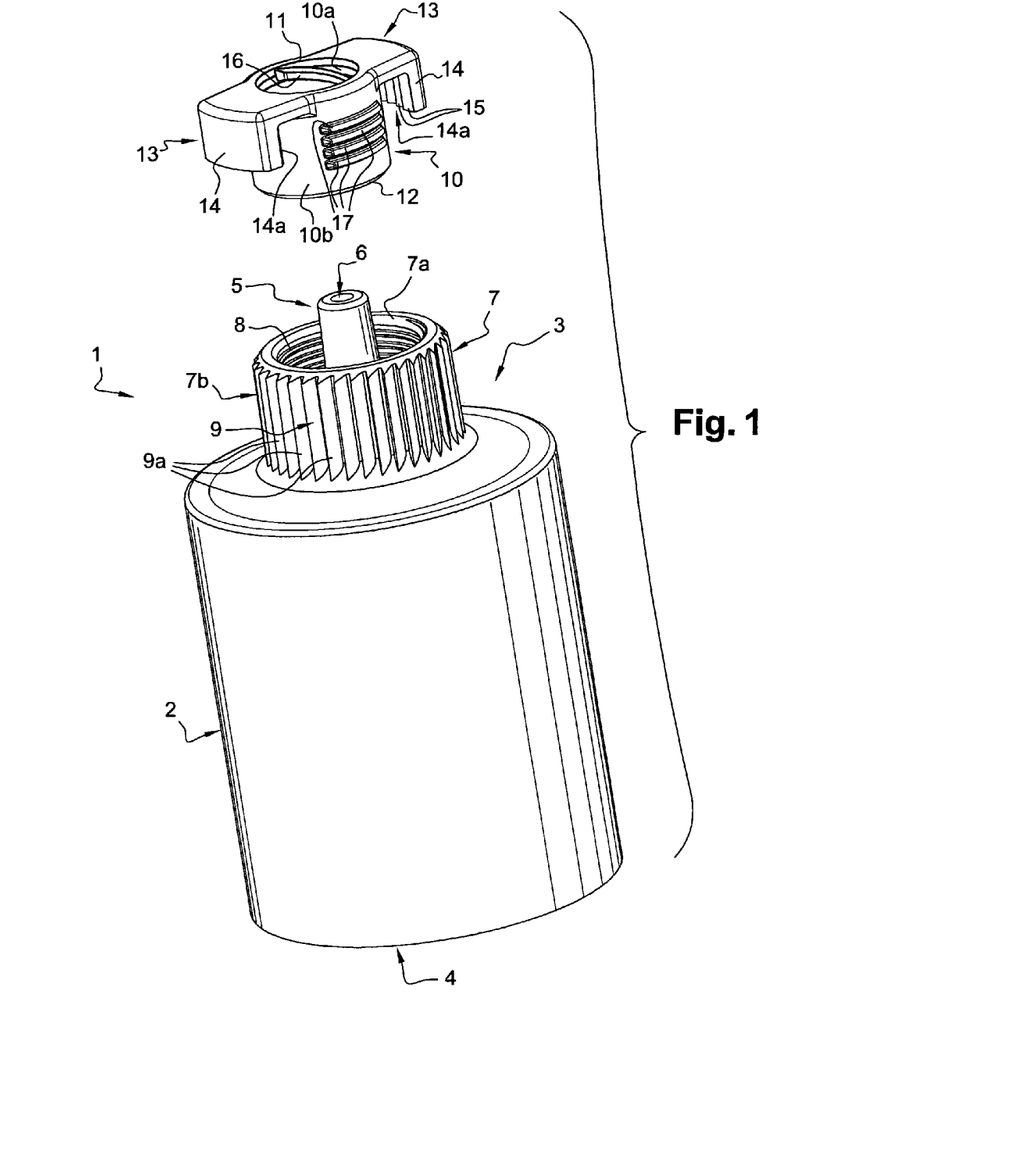
FIG. 1 is a perspective view of a first embodiment of the device of the invention, before fixation of the connection means on the distal end of the reservoir.
Figure 2:
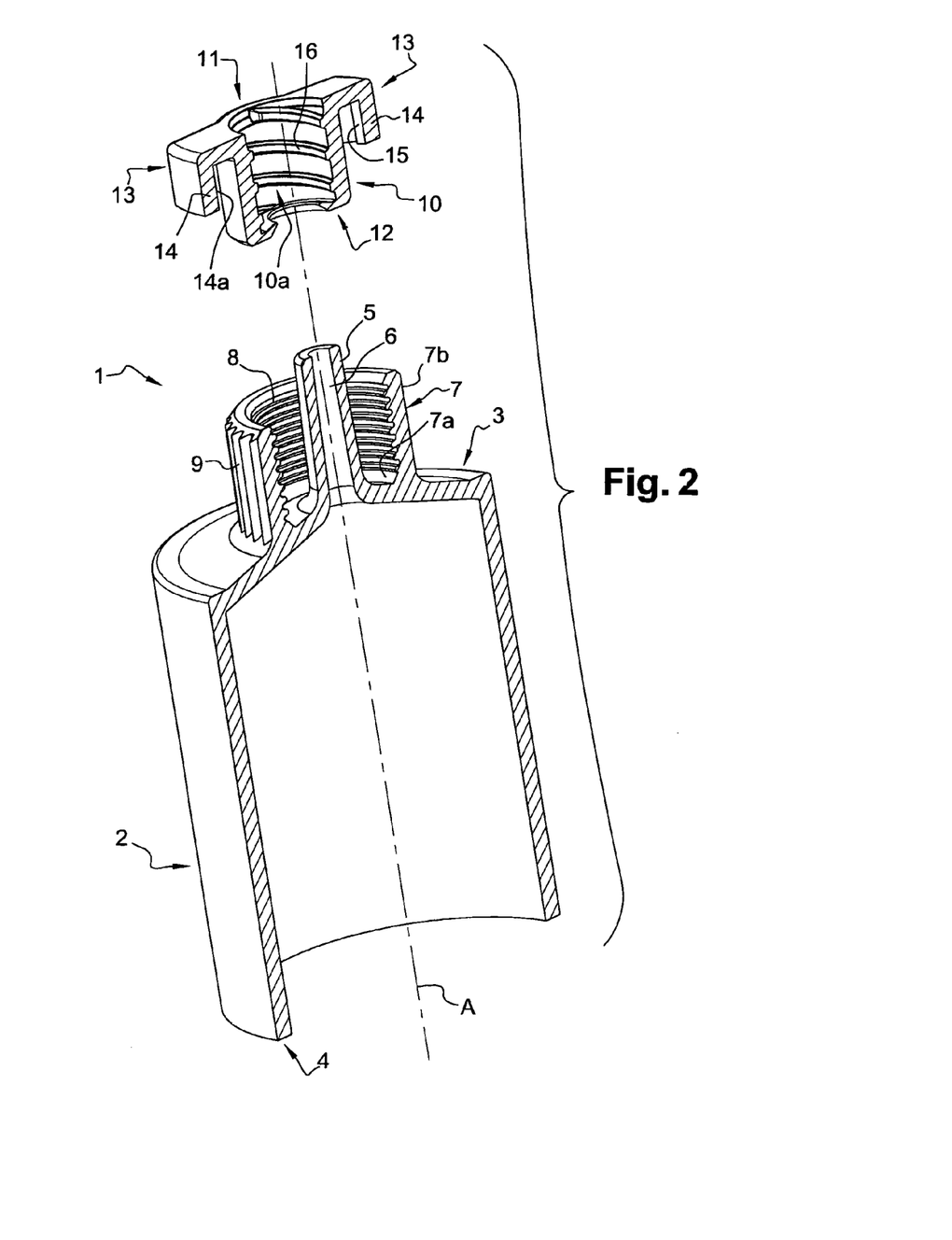
FIG. 2 is cross section view of the device of FIG. 1.

With reference to FIGS. 1 and 2 is shown a drug delivery device 1 of the invention intended to deliver a product (not shown) to a patient. In this view, the drug delivery device 1 is intended to be coupled to a connector (not shown) such as IV (Intra Veinous) connectors which usually link drug delivery devices, containing the product to be delivered, to IV lines which are themselves directly connected to the vein of the patient.

With reference to FIG. 1, the drug delivery device 1 comprises a reservoir 2 for carrying a product to be delivered to a patient, like a medicinal substance. The reservoir 2 may be any container such as a vial, catheter or a syringe barrel for example. The reservoir 2 has a distal end 3 and a proximal end 4: in the case the reservoir is a syringe barrel, the proximal end 4 is usually open. The distal end 3 of the reservoir 2 comprises an end-piece 5 having a longitudinal axis A (see FIG. 2): the end-piece 5 has a global shape of a tube and it is traversed by a channel 6 aligned on said longitudinal axis A and providing a passageway for the transfer of the product, from the reservoir 2 to the exterior, and in particular to the IV line, as will be explained later.

On the embodiment shown on FIGS. 1 and 2, the end-piece 5 is surrounded with a collar 7 extending from the the distal end 3 of the reservoir 2. On the example shown, the internal face 7a of the collar 7 is provided with a thread 8, the function of which will be explained later. On its external face 7b, the collar 7 is provided with a plurality of longitudinal ridges 9, running on the whole circumference of the collar 7: all the longitudinal ridges 9 have each a sloped surface 9a, all the sloped surfaces 9a being parallel to each other.

On the example shown on FIGS. 1 and 2, the reservoir 2, the end-piece 5 and the collar 7 are made of one single piece; in other embodiments not shown, the end-piece and/or the collar could be made separately from the reservoir and then fixed, for example by gluing, to the distal end 3 of the reservoir.

When the reservoir 2, the end-piece 5 and the collar 7 are made of one single piece as shown on FIGS. 1 and 2, said single piece may be produced by injection molding and may be made for example of a material selected from cycloolefin polymers, cycloolefin copolymers and mixtures thereof. Such a material being a plastic material, it has the advantage over glass that is is less dangerous if it happens to break. Moreover, such a material shows a high transparency for visual control of the drug and a high geometrical stability when it is subjected to high pressure in the reservoir: this is particularly useful when the reservoir is a syringe barrel.

The drug delivery device 1 of FIGS. 1 and 2 further comprises a tubular wall 10 having a distal end 11 and a proximal end 12. The distal end 11 is provided with two opposite outer ears 13, each provided with a proximal skirt 14, and forming a discontinuous ring linked to the tubular wall 10. The inner face 14a of each skirt 14 is provided with longitudinal projections 15.

In an embodiment not shown, the outer ears could run all along the circumference of the tubular wall and they could form a continuous ring linked to the tubular wall.

The inner face 10a of the tubular wall 10 is provided with a thread 16. The outer face 10b of the tubular wall 10 is provided with four outer rims 17 regularly spaced one from the other in the axial direction and defining an interface of said tubular wall 10 for engagement with an internal face 7a of the collar 7: as will appear from the description below, the space separating each outer rim 17 from the adjacent outer rim 17 corresponds to the screw thread of the thread 8 of the internal face 7a of the collar 7. As a result, the interface of the tubular wall 10, i.e. the outer rims 17, defines screwing means.

On the example shown on FIGS. 1 to 4, the tubular wall 10 is fixed to the distal end 3 of the reservoir 2 by screwing said tubular wall 10 into the collar 7. In this view, the proximal end 12 of the tubular wall 10 is engaged in the collar 7; during the screwing step, the four outer rims 17 cooperate with the thread 8 of the collar 7. During this step also, the longitudinal projections 15 of the inner face 14a of each skirt 14 cooperate with the longitudinal ridges 9, and in particular with the sloped surfaces 9a, in order to allow the movement of the tubular wall 10 with respect to the collar 7 in the screwing direction and to prevent such movement in the unscrewing direction.

Figure 3:
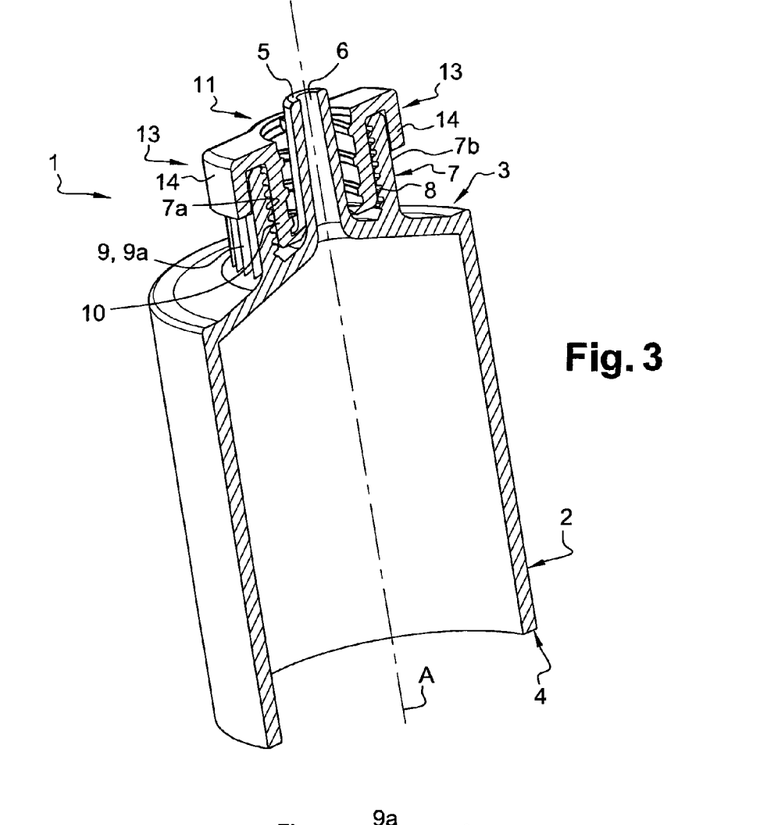
FIG. 3 is a cross section view of the device of FIG. 1 once the connection means are fixed to the distal end of the reservoir.
Figure 4:
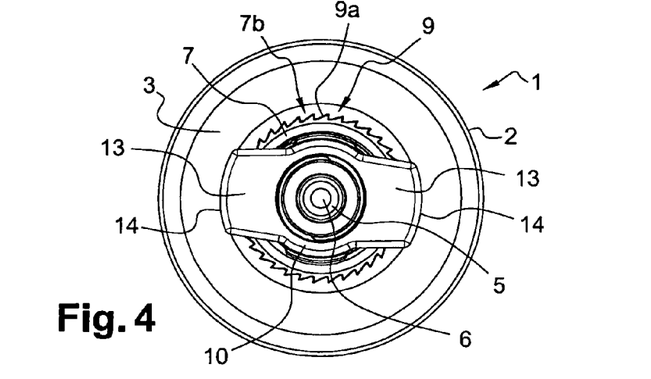
FIG. 4 is a top view of the device of FIG. 3.

At the end of the screwing step, the tubular wall 10 is therefore definitely connected to the collar 7, as shown on FIGS. 3 and 4. The longitudinal projections 15 form engagement means engageable with at least part of the external face of the collar 7. The cooperation of the longitudinal projections 15 and of the sloped surfaces 9a of the longitudinal ridges 9 forms stopping means for preventing the tubular wall 10 from being unscrewed or threadedly removed from the collar 7. Also, in this configuration, the tubular wall 10 is prevented from moving in the axial direction with respect to the collar 7.

When the tubular wall 10 is connected to the collar 7, as shown on FIG. 3, the interface of the tubular wall 10, in other words the outer rims 17, is engaged with the internal face 7a of the collar 7. Moreover, in this position also, the longitudinal projections 15 of the inner face 14a of the skirts 14 of the ears 13 are engaged with at least part of the distal region of the external face 7b of the collar 7 and they form a retaining hook able to absorb part of the force which will be applied on the distal end 3 of the reservoir when the connector is coupled thereto. The retaining hook and the tubular wall therefore form connection means to be connected to the collar, for coupling a connector to the end-piece of the drug delivery device.

As a consequence, the collar 7 is particularly well protected and reinforced, and the distal end 3 of the reservoir 2 is ready to receive a connector (not shown) intended to be coupled thereto in order to further complete the transfer of the product to the IV line, via the connector. Usually, the connector will be provided with an external thread able to cooperate with the thread 16 of the inner face 10a of the tubular wall 10.

In particular, because the tubular wall 10 is preferably made of a material selected from polyolefines, for example selected in the group comprising polyethylene, linear low density polyethylene, polypropylene and mixtures thereof, its integrity may not affected by an inadvertent dripping of product further to the completion of a purge of the reservoir 2 by the user.

Also, the outer rims 17 provide reinforcement to the collar 7, which is more resistant and may not break at the time the connector is connected or disconnected to the distal end 3 of the reservoir 2.

As a consequence, the tubular wall 10 forms part of a connection means for coupling a connector to the end-piece 5 of the drug delivery device 1, the structure of which allows the coupling and the uncoupling of said connector onto the end-piece with very limited risks that the collar breaks: in particular, whatever the force applied on the distal end of the drug delivery device 1 when the connector is screwed within the tubular wall 10, the connection means, in other words the tubular wall 10 and the retaining hook formed of the ears 13 and skirts 14, absorb the stress applied and prevent the collar 7 from being damaged or or from breaking.

Figure 5:
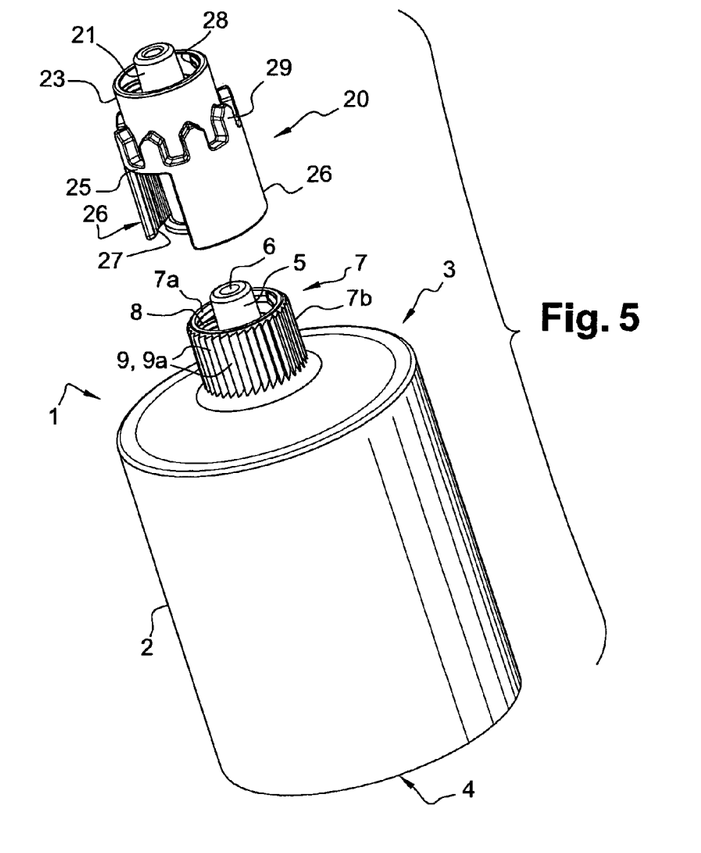
FIG. 5 is a perspective view of a second embodiment of the device of the invention, before fixation of the connection means on the distal end of the reservoir.
Figure 6:
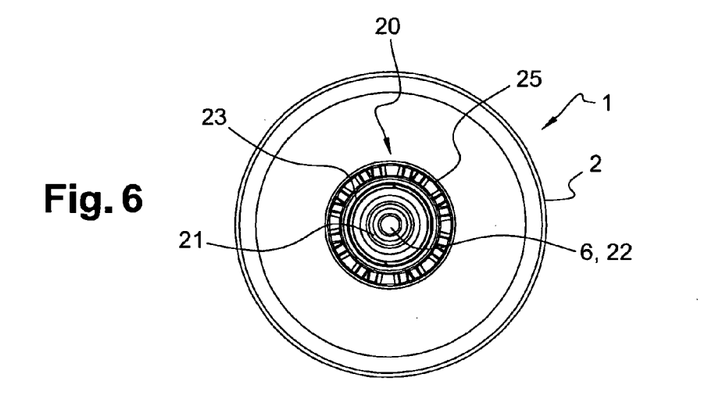
FIG. 6 is a top view of the device of FIG. 5 once the connection means are fixed on the distal end of the reservoir.
Figure 7:
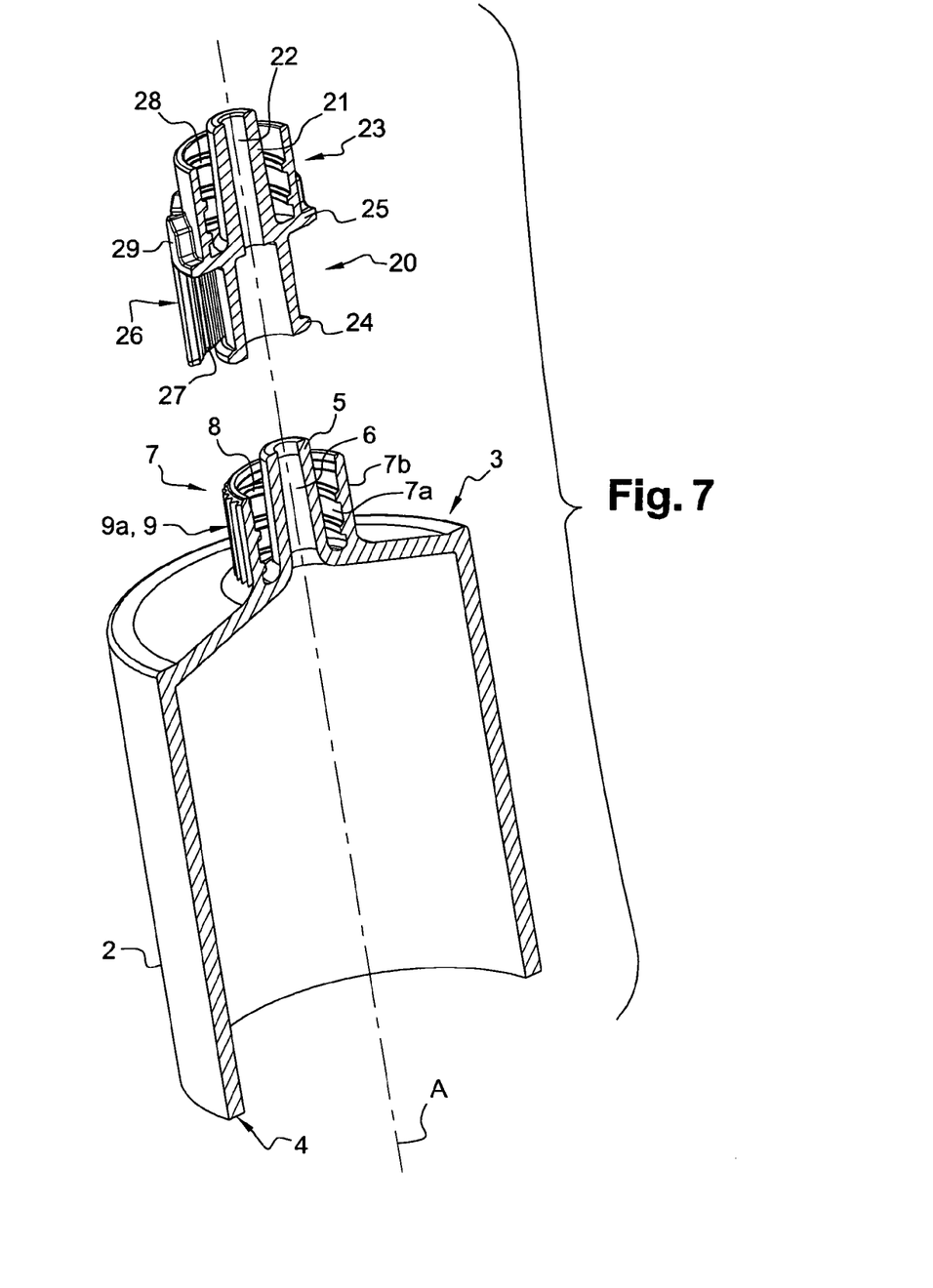
FIG. 7 is a cross section view of the device of FIG. 5.

With reference to FIGS. 5-7 is shown a second embodiment of the drug delivery device 1 of the invention. In this embodiment, the reservoir 2 is identical to that of FIGS. 1-4 and the same references have been maintained.

In the embodiment of these Figures, the drug delivery device 1 is provided with a tubular wall 20 which is prolonged in the distal direction with a longitudinal tip 21 provided with a duct 22 aligned on said longitudinal axis A of said end-piece 5, and by an outer ring 23 surrounding said tip 21.

At its proximal end, the tubular wall 20 is provided with an outer flange 24 defining an interface of said tubular wall 20, screwing means in the example shown, able to cooperate with the thread 8 of the collar 7. The tubular wall 20 is also provided with an outer annular wall 25 provided with two opposite skirts 26 extending in the proximal direction. The inner face of the skirts 26 are provided with longitudinal projections 27 able to cooperate with the longitudinal ridges 9 and their sloped surfaces 9a in order to allow the screwing movement of the tubular wall 20 into the collar 7 and to prevent the unscrewing movement of the tubular wall 20 from the collar 7, in the same manner as described for the embodiment of FIGS. 1-4. The longitudinal projections 27 therefore form engagement means engageable with at least part of the external face of the collar 7. The annular wall 25 is further provided with outer projections 29 extending in the distal direction and forming gripping surfaces for the fingers of the user at the time of threadedly connecting the tubular wall 20 within the collar 7.

The outer ring 23 is provided on its inner face with a thread 28 intended to cooperate with an external thread of the connector (not shown) intended to be coupled to the distal end 3 of the reservoir 2 via the connection means formed partly by the tubular wall 20.

Once the tubular wall 20 is threadedly connected to the collar 7, the two passage ways, i.e. the channel 6 and the duct 22, respectively of the end-piece 5 and of the tip 21, are aligned (see FIG. 6) and will allow the product to be transferred from the reservoir 2 to the IV line through the connector, once said connector is connected to the distal end 3 of the reservoir via the tubular wall 20.

Like for the embodiment of FIGS. 1-4, when the tubular wall 20 is connected to the collar 7, the interface of the tubular wall 20, in other words the flange 24, is engaged with the internal face 7a of the collar 7. Moreover, in this position also, the longitudinal projections 27 of the skirts 26 are engaged with at least part of the distal region of the external face 7b of the collar 7 and they form a retaining hook able to absorb part of the force which will be applied on the distal end 3 of the reservoir 2 when the connector is coupled thereto. The retaining hook and the tubular wall therefore form connection means to be connected to the collar, for coupling a connector to the end-piece of the drug delivery device.

In particular, because the tubular wall 20 is preferably made of of a material selected from polyolefines, for example selected in the group comprising polyethylene, linear low density polyethylene, polypropylene and mixtures thereof, its integrity may not affected by an inadvertent dripping of product further to the completion of a purge of the reservoir 2 by the user.

The tubular wall 20 therefore forms part of connection means for coupling a connector to the end-piece 5 of the drug delivery device 1, the structure of which allows the coupling and the uncoupling of said connector onto the end-piece with very limited risks that the collar breaks: in particular, whatever the force applied on the distal end 3 of the drug delivery device 1 when the connector is screwed within the tubular wall 20, the connection means, in other words the tubular wall 20 and the retaining hook formed of the skirts 26, absorb the stress applied and prevent the collar 7 from being damaged or or from breaking.

The present invention therefore provides for a drug delivery device having an end-piece surrounded by a collar, with very limited risks that the collar breaks either at the time the connector is coupled to, or uncoupled from, the end-piece, or during use, regardless of the variation of intensity of the force that may be applied by a user for completing the connection step and regardless of the fact that the collar may have been contacted by a potential degrading product before the connection step.

The invention claimed is:

1. A drug delivery device for containing a product comprising:
   a main portion comprising:
   a reservoir;
   an end-piece defining a channel providing a passageway for the transfer of the product from the reservoir; and
   a collar for coupling the end-piece with a connector, the collar defined around a portion of the end-piece and extending from a distal end of the main portion, an external surface of the collar having longitudinal ridges running from a proximal end of the collar to the distal end of the collar; and
   a connector comprising:
   a tubular wall portion having an interface defined thereon for engagement with an internal surface of the collar; and
   a retaining hook having longitudinal projections engageable with at least part of the longitudinal ridges on the external surface of the collar when the connector is connected to the collar.

2. A drug delivery device defining a reservoir for containing a product, said drug delivery device having a distal end comprising an end-piece defining a channel providing a passageway for the transfer of the product from the reservoir, said drug delivery device comprising coupling means for coupling said end-piece with a connector, said coupling means comprising a collar defined around a portion of the end-piece and extending from the distal end, said coupling means further comprising connection means connectable to said collar and for coupling the end-piece with a connector, said connection means comprising a tubular wall portion having an interface defined thereon for engagement with an internal face of said collar, said connection means further comprising a retaining hook having first engagement means engageable with at least part of a second engagement means on an external face of said collar when said connection means is connected to said collar, wherein the second engagement means comprises longitudinal ridges extending from a proximal end of the collar to a distal end of the collar.

3. The drug delivery device according to claim 2, wherein said connection means is made of a polyolefines material selected from the group comprising polyethylene, linear low density polyethylene, polypropylene and mixtures thereof.

4. The drug delivery device according to claim 2, wherein said interface is selected from the group consisting of overmoulding means, snap-fastening means, screwing means, welding means, force fitting means and combinations thereof.

5. The drug delivery device according to claim 2, wherein said collar is made of a material selected from cycloolefin polymers, cycloolefin copolymers and mixtures thereof.

6. The drug delivery device according to claim 2, wherein said retaining hook is a discontinuous ring extending from said tubular wall and covering part of the distal region of the outer face of the collar, when said connection means is connected to said collar.

7. The drug delivery device according to claim 2, wherein said retaining hook is a continuous ring extending from said tubular wall and covering the distal region of the outer face of the collar, when said connection means is connected to said collar.

8. The drug delivery device according to claim 2, wherein the inner face of said collar has a thread defined thereon engageable with said interface.

9. The drug delivery device according to claim 2, wherein said connection means further comprises a tip having a duct defined therethrough, and an outer ring defined around said tip, said duct being axially aligned with said channel when said connection means is connected to said collar.

10. The drug delivery device according to claim 9, wherein the inner face of said outer ring has a thread defined thereon.

11. The drug delivery device according to claim 2, wherein said connection means is threadedly connectable with said collar.

12. The drug delivery device according to claim 2, wherein said external face has defined therein longitudinal ridges having sloped surfaces engageable with longitudinal projections defined on the retaining hook, so as to allow said connection means to be threadedly connected to said collar, and so as to prevent said connection means from being threadedly removed from said collar.

13. The drug delivery device according to claim 2, wherein said reservoir, end-piece and collar are unitarily formed from a material selected from cycloolefin polymers, cycloolefin copolymers and mixtures thereof.

* * * * *

UNITED STATES PATENT AND TRADEMARK OFFICE
CERTIFICATE OF CORRECTION

PATENT NO. : 8,882,726 B2  Page 1 of 1
APPLICATION NO. : 13/583352
DATED : November 11, 2014
INVENTOR(S) : Catherine Felix-Faure et al.

It is certified that error appears in the above-identified patent and that said Letters Patent is hereby corrected as shown below:

In the Claims

Column 8, Line 61, Claim 3, delete "polyolefines" and insert -- polyolefins --

Column 8, Lines 65-66, Claim 4, delete "overmoulding" and insert -- overmolding --

Signed and Sealed this
Fourteenth Day of April, 2015

Michelle K. Lee
*Director of the United States Patent and Trademark Office*